United States Patent
Gandhi et al.

(10) Patent No.: US 8,868,187 B2
(45) Date of Patent: Oct. 21, 2014

(54) BATTERY DEPTH OF DISCHARGE IN AN IMPLANTABLE DEVICE

(75) Inventors: Rajesh K. Gandhi, Woodbury, MN (US); Michael J. Root, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 942 days.

(21) Appl. No.: 12/486,434

(22) Filed: Jun. 17, 2009

(65) Prior Publication Data

US 2009/0312809 A1 Dec. 17, 2009

Related U.S. Application Data

(60) Provisional application No. 61/073,195, filed on Jun. 17, 2008.

(51) Int. Cl.
| | |
|---|---|
| *A61N 1/08* | (2006.01) |
| *H02J 7/04* | (2006.01) |
| *A61N 1/37* | (2006.01) |
| *A61N 1/378* | (2006.01) |

(52) U.S. Cl.
CPC ............. *A61N 1/3708* (2013.01); *A61N 1/378* (2013.01); *A61N 1/08* (2013.01)
USPC ........................................................ 607/29

(58) Field of Classification Search
USPC ........................................................ 607/29
See application file for complete search history.

(56) References Cited

U.S. PATENT DOCUMENTS

| | | |
|---|---|---|
| 4,332,256 A | 6/1982 | Brownlee et al. |
| 4,416,282 A | 11/1983 | Saulson et al. |
| 4,556,061 A | 12/1985 | Barreras et al. |
| 4,715,381 A | 12/1987 | Moberg |
| 5,031,616 A | 7/1991 | Mann et al. |

(Continued)

FOREIGN PATENT DOCUMENTS

| | | |
|---|---|---|
| EP | 1038498 A2 | 9/2000 |
| EP | 1610437 A1 | 12/2005 |

(Continued)

OTHER PUBLICATIONS

"U.S. Appl. No. 12/277,091, Final Office Action mailed Sep. 14, 2011", 25 pgs.

(Continued)

*Primary Examiner* — Tammie K Heller
(74) *Attorney, Agent, or Firm* — Schwegman Lundberg & Woessner, P.A.

(57) ABSTRACT

Systems and methods for determining depth of discharge for implantable device batteries are provided. One aspect of this disclosure relates to a method for determining depth of discharge for a battery in an implantable medical device. Voltage recovery of the battery is measured subsequent to a predetermined event. Measured voltage recovery data is stored in a database adapted to store data for one or more devices. Measured voltage recovery data is compared with stored voltage recovery data to determine battery depth of discharge. According to various embodiments, battery capacity consumed is measured using a coulometer and using a capacity-by-voltage device. Measured battery capacity consumed is combined with measured voltage recovery data using a predetermined weighted average, and the combined data is stored in the database. The stored data is used to determine battery depth of discharge, according to an embodiment.

20 Claims, 12 Drawing Sheets

(56) References Cited

U.S. PATENT DOCUMENTS

| | | |
|---|---|---|
| 5,137,020 A | 8/1992 | Wayne et al. |
| 5,313,953 A | 5/1994 | Yomtov et al. |
| 5,325,041 A | 6/1994 | Briggs |
| 5,344,431 A | 9/1994 | Merritt et al. |
| 5,391,193 A | 2/1995 | Thompson |
| 5,432,429 A | 7/1995 | Armstrong, II et al. |
| 5,458,624 A | 10/1995 | Renirie et al. |
| 5,620,474 A | 4/1997 | Koopman |
| 5,713,936 A | 2/1998 | Staub |
| 5,741,307 A | 4/1998 | Kroll |
| 5,769,873 A | 6/1998 | Zadech |
| 5,800,472 A | 9/1998 | Mann |
| 5,904,705 A | 5/1999 | Kroll et al. |
| 5,931,791 A | 8/1999 | Saltzstein et al. |
| 6,108,579 A | 8/2000 | Snell et al. |
| 6,148,235 A | 11/2000 | Kuiper |
| 6,167,309 A | 12/2000 | Lyden |
| 6,185,461 B1 | 2/2001 | Er |
| 6,377,850 B1 * | 4/2002 | Takeuchi et al. ............ 607/2 |
| 6,400,988 B1 | 6/2002 | Gurewitsch |
| 6,438,409 B1 | 8/2002 | Malik et al. |
| 6,531,874 B2 | 3/2003 | Mentgen et al. |
| 6,621,250 B1 | 9/2003 | Ohkubo et al. |
| 6,671,552 B2 | 12/2003 | Merritt et al. |
| 6,760,625 B1 | 7/2004 | Kroll |
| 6,885,894 B2 | 4/2005 | Stessman |
| 6,901,293 B2 | 5/2005 | Rogers et al. |
| 6,940,255 B2 | 9/2005 | Loch |
| 7,058,451 B2 | 6/2006 | Obel et al. |
| 7,072,725 B2 | 7/2006 | Bristol et al. |
| 7,177,690 B2 | 2/2007 | Woods et al. |
| 7,194,308 B2 | 3/2007 | Krig et al. |
| 7,221,977 B1 | 5/2007 | Weaver et al. |
| 7,239,146 B2 | 7/2007 | James et al. |
| 7,450,991 B2 | 11/2008 | Smith et al. |
| 8,055,343 B2 | 11/2011 | Gandhi et al. |
| 2001/0034541 A1 | 10/2001 | Lyden |
| 2002/0143580 A1 | 10/2002 | Bristol et al. |
| 2003/0065366 A1 | 4/2003 | Merritt et al. |
| 2003/0149455 A1 | 8/2003 | Obel et al. |
| 2004/0039424 A1 | 2/2004 | Merritt et al. |
| 2004/0199146 A1 | 10/2004 | Rogers et al. |
| 2005/0102005 A1 | 5/2005 | Krig et al. |
| 2005/0256548 A1 | 11/2005 | Rogers et al. |
| 2005/0266301 A1 | 12/2005 | Smith et al. |
| 2005/0277994 A1 | 12/2005 | McNamee et al. |
| 2006/0176022 A1 | 8/2006 | Namba |
| 2006/0220619 A1 | 10/2006 | Namba et al. |
| 2007/0150018 A1 | 6/2007 | Betzold et al. |
| 2008/0097544 A1 | 4/2008 | Gandhi et al. |
| 2009/0182517 A1 | 7/2009 | Gandhi et al. |

FOREIGN PATENT DOCUMENTS

| | | |
|---|---|---|
| WO | WO-01/05466 A1 | 1/2001 |
| WO | WO-01/08749 A1 | 2/2001 |
| WO | WO-02/49718 A1 | 6/2002 |
| WO | WO-2004/091697 A1 | 10/2004 |

OTHER PUBLICATIONS

"U.S. Appl. No. 12/277,091, Pre-Appeal Brief Request for Review", 5 pgs.

"U.S. Appl. No. 11/551,269, Non-Final Office Action mailed Mar. 30, 2010", 12 pgs.

"U.S. Appl. No. 11/551,269, Response filed Jun. 30, 2010 to Non Final Office Action mailed Mar. 30, 2010", 9 pgs.

U.S. Appl. No. 11/551,269, Restriction Requirement mailed Feb. 10, 2009, 10 pgs.

U.S. Appl. No. 11/551,269, Advisory Action mailed Mar. 4, 2010, 3 pgs.

U.S. Appl. No. 11/551,269, Final Office Action mailed Nov. 24, 2009, 12 pgs.

U.S. Appl. No. 11/551,269, Non-Final Office Action mailed May 12, 2009, 8 pgs.

U.S. Appl. No. 11/551,269, Response filed Feb. 17, 2010 to Final Office Action mailed Nov. 24, 2009, 9 pgs.

U.S. Appl. No. 11/551,269, Response filed Mar. 12, 2009 to Restriction Requirement mailed Feb. 10, 2009, 6 pgs.

U.S. Appl. No. 11/551,269, Response filed Aug. 11, 2009 to Non-Final Office Action mailed May 12, 2009, 10 pgs.

International Application Serial No. PCT/US2008/013059, International Search Report mailed May 27, 2009, 4 pgs.

International Application Serial No. PCT/US2008/013059, Written Opinion mailed May 27, 2009, 7 pgs.

U.S. Appl. No. 11/511,269, Notice of Allowance mailed Aug. 22, 2011, 13 pgs.

U.S. Appl. No. 11/551,269, Final Office Action mailed Oct. 7, 2010, 12 pgs.

U.S. Appl. No. 11/551,269, Non Final Office Action mailed Mar. 3, 2011, 14 pgs.

U.S. Appl. No. 11/551,269, Response filed Jan. 6, 2011 to Final Office Action mailed Oct. 7, 2010, 10 pgs.

U.S. Appl. No. 11/551,269, Response filed Jun. 3, 2011 to Non Final Office Action mailed Mar. 3, 2011, 10 pgs.

U.S. Appl. No. 12/277,091, Non Final Office Action mailed Mar. 25, 2011, 21 pgs.

U.S. Appl. No. 12/277,091, Response filed Jun. 27, 2011 to Non-Final Office Action mailed Mar. 25, 2011, 14 pgs.

U.S. Appl. No. 12/277,091, Decision on Pre-Appeal Brief mailed Feb. 15, 2012, 2 pgs.

U.S. Appl. No. 12/277,091, Notice of Allowance mailed Mar. 5, 2012, 8 pgs.

U.S. Appl. No. 13/287,824, Final Office Action mailed Sep. 13, 2012, 14 pgs.

U.S. Appl. No. 13/287,824, Response filed Aug. 10, 2012 to Non Final Office Action mailed May 10, 2012, 10 pgs.

\* cited by examiner

FIG. 8A

BATTERY DEPTH OF DISCHARGE IN AN IMPLANTABLE DEVICE

CROSS REFERENCE TO RELATED APPLICATION

This application claims the benefit of U.S. Provisional Application No. 61/073,195, filed on Jun. 17, 2008, under 35 U.S.C. § 119(e), which is hereby incorporated by reference.

This application is related to the following commonly assigned U.S. patent applications which are herein incorporated by reference in their entirety: "Dynamic Battery Management in an Implantable Device," Ser. No. 11/551,269, filed Oct. 20, 2006, now issued as U.S. Pat. No. 8,055,343; and "Abnormal Battery Depletion Detection in an Implantable Device," provisional U.S. patent application Ser. No. 61/007,636, filed on Dec. 13, 2007.

TECHNICAL FIELD

This disclosure relates generally to implantable devices, and more particularly to systems and methods for determining depth of discharge for implantable device batteries.

BACKGROUND

Implantable medical devices include, among other things, cardiac rhythm management (CRM) devices such as pacers, cardioverters, defibrillators, cardiac resynchronization therapy (CRT) devices, as well as combination devices that provide more than one of these therapy modalities to a subject. Such implantable devices are typically powered by a battery. When the battery's useful life has been exhausted, the implanted device is typically explanted and replaced before the cessation of therapy. Therefore, it is often useful to know how much battery capacity has been used and/or how much battery capacity remains. Improved systems and methods for battery management and determining depth of discharge for batteries in implantable medical devices are needed.

SUMMARY

The above-mentioned problems and others not expressly discussed herein are addressed by the present subject matter and will be understood by reading and studying this specification.

Disclosed herein, among other things, is a system for determining depth of discharge for batteries in implantable medical devices. One embodiment of the system includes at least one voltage sensor adapted to sense voltage of the battery and a memory adapted to store voltage recovery data subsequent to a voltage discharge event from one or more implantable devices. The system also includes a controller connected to the memory and in communication with the implantable medical device. The controller is adapted to measure voltage recovery based on sensed voltage, to store voltage recovery data in the memory, and to compare measured voltage recovery data with stored voltage recovery data to determine battery depth of discharge.

One aspect of this disclosure relates to a method for determining depth of discharge for a battery in an implantable medical device. Voltage recovery of the battery is measured subsequent to a predetermined event. Measured voltage recovery data is stored in a database adapted to store data for one or more devices. Measured voltage recovery data is compared with stored voltage recovery data to determine battery depth of discharge. According to various embodiments, battery capacity consumed is measured using a coulometer and using a capacity-by-voltage device. Measured battery capacity consumed is combined with measured voltage recovery data using a predetermined weighted average, and the combined data is stored in the database. The stored data is used to determine battery depth of discharge, according to an embodiment.

One aspect of this disclosure relates to a method for determining capacity consumed for a battery in an implantable medical device. Battery capacity consumed is measured using voltage recovery as an indication of depth of depletion of the battery. Battery capacity consumed is also measured using a coulometer. Battery capacity consumed is further measured using a capacity-by-voltage device. The measurements from voltage recovery and at least one of the coulometer and the capacity-by-voltage device are combined using a weighted average to determine battery capacity consumed data.

This summary is an overview of some of the teachings of the present application and not intended to be an exclusive or exhaustive treatment of the present subject matter. Further details about the present subject matter are found in the detailed description and appended claims. Other aspects will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

FIGS. 8A-8E illustrate screen displays for the system of FIG. 3, used to display battery longevity, according to one embodiment.

DETAILED DESCRIPTION

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

Various embodiments of the present subject matter are related to implantable medical device battery management. Displaying the remaining battery capacity in amp/hours can cause a misunderstanding by users, as users may believe it represents the amount of time remaining rather than the amount of charge remaining.

In various embodiments, the present subject matter includes a system for measuring consumed battery capacity. In various embodiments, this system includes blending multiple independent measurements of battery capacity. In some embodiments, the system includes a display and battery longevity is displayed in units of time left in the life of the battery. The present disclosure can be used with a variety of implantable device batteries, including by not limited to: SVO (Silver Vanadium Pentoxide), $MnO_2$ (Lithium Manganese Dioxide), CFx (Lithium Carbon Monofluoride) and hybrid SVO and CFx batteries.

System for Dynamic Battery Management

Figure 1:
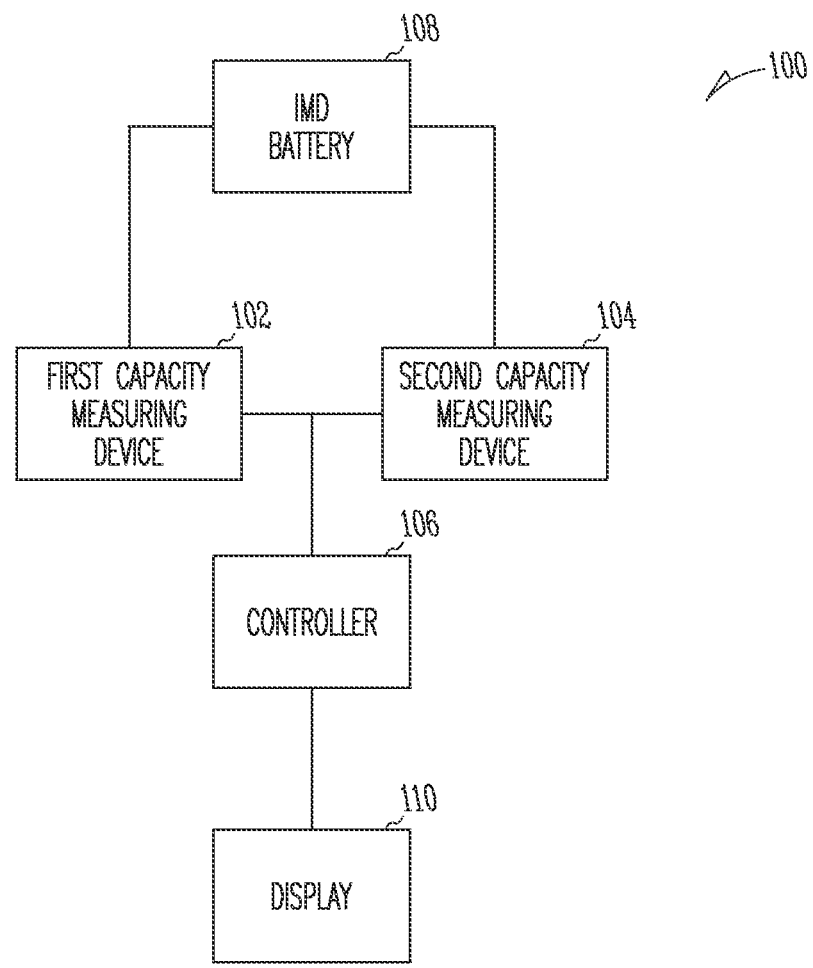
FIG. 1 illustrates a block diagram of a system for dynamic battery management, according to one embodiment.

FIG. 1 illustrates a block diagram of a system for dynamic battery management, according to one embodiment. One embodiment of the system 100 includes two or more devices (102, 104) for measuring battery capacity for an implantable medical device battery 108. The embodiment also includes a controller 106 connected to the measuring devices. The controller 106 is adapted to combine the measurements from the measuring devices (102, 104) using a weighted average to determine battery capacity consumed. According to various embodiments, at least one of the measuring devices includes a coulometer (or Coulomb counter). At least one of the measuring devices includes a capacity-by-voltage device, according to an embodiment. A capacity-by-voltage device detects a voltage level and outputs a battery capacity using, for instance, a look-up table. In one embodiment, at least one of the measuring devices includes a software coulometer. According to various embodiments, the software coulometer tallies every system event (such as a shock or pace sequence), duration of the event and multiply using a look-up table of cost (energy used in amperes, or amps). The accumulation of events, duration and cost would result in capacity consumed, units of Ahr. In varying embodiments, at least one of the measuring means devices a charge-time measuring device. A charge-time measuring device can be used in as system including a defibrillator, because in a defibrillator system charge-time can directly be related to battery internal impedance. The voltage drop from open-circuit to loaded for a high voltage (HV) capacitor charge divided by the loaded current is the internal impedance ($R=\Delta V/\Delta I$). From a look-up table, the internal impedance can be mapped to capacity consumed, according to an embodiment. The system further includes a display 110 in communication with the controller in various embodiments. The display 110 is adapted to provide a depiction of battery longevity in units of time remaining in the life of the implantable medical device battery, according to various embodiments.

According to various embodiments, the system of FIG. 1 is adapted to dynamically manage an implanted device. In previous systems, a static explant capacity is allocated at design-time for a heavy usage scenario (i.e. 5% of a device's capacity will remain at the explant indicator). That capacity is designed to offer at least 90 days of heavy usage therapy before cessation. In the present system, using dynamic allocation, the device actively measures long-term power consumption and allocates post-explant capacity. In this manner, low-usage devices will have less reserve capacity but longer total longevity. High-usage devices will have more post-explant reserve capacity and less total longevity. This strategy maximizes individual longevity and minimizes risk of cessation before replacement.

When using a capacity-by-voltage device, a look-up table is indexed by power and voltage to obtain capacity consumed, in varying embodiments. The capacity-by-voltage device utilizes at least one voltage measuring device, according to an embodiment. Accuracy of the capacity-by-voltage device is best near ERI, but may be unusable before significant (70% depleted, or approximately 30% remaining) battery depletion, because many batteries have flat or rising voltage profiles early in life (see FIG. 7, discussed below).

When using a coulometer, or Coulomb counter, the device can include one of a number of standard devices, and measures voltage across a known resistance and computes current. The current is integrated over time with a result of amp-seconds, or coulombs, a measure of charge. Capacity consumed is constantly measured by the coulometer, in various embodiments. According to an embodiment, the coulometer is calibrated to an accuracy of +/−10% or better. Absolute accuracy of the coulometer is most useful early in battery life.

Figure 5:
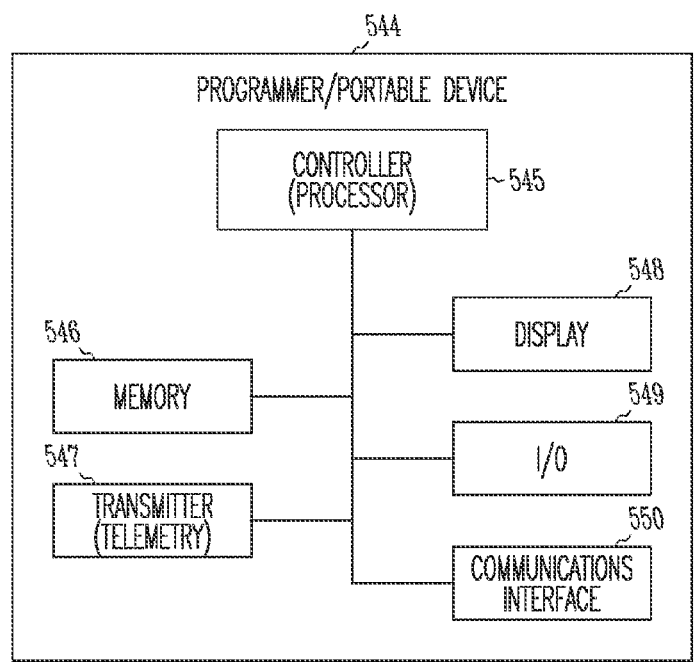
FIG. 5 illustrates a block diagram of a programmer such as illustrated in the system of FIG. 4 or other external device to communicate with the IMD(s), according to one embodiment.

According to various embodiments, the capacity measuring devices (102, 104) are located within the implantable medical device (IMD). According to an embodiment, the controller is located within the IMD. In this embodiment, measurement and blending of the measured data are completed within the IMD, and both raw and blended data are reported to an external device having display 110. An embodiment of the external device is shown in FIG. 5. In one embodiment, the depiction of battery longevity provided by the display includes a semicircular gauge. In another embodiment, the depiction of battery longevity includes a graph.

Figure 2:
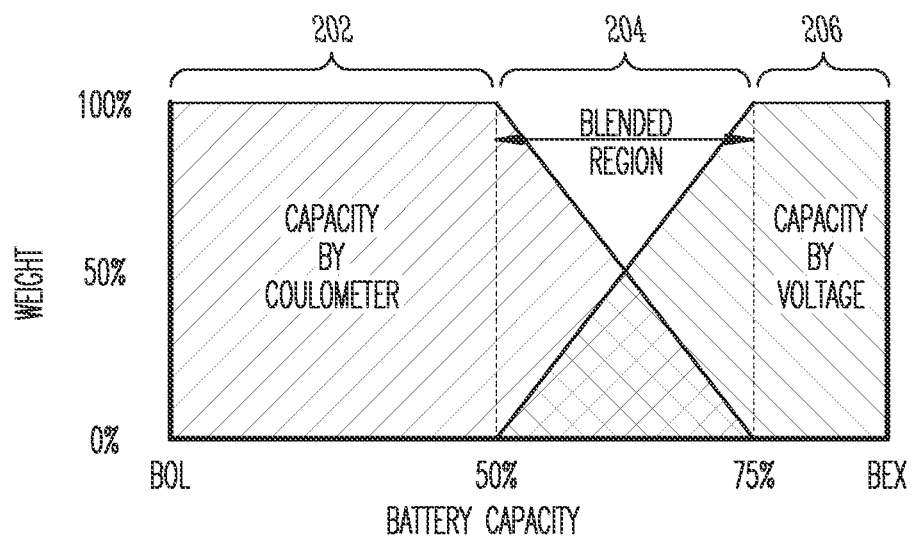
FIG. 2 illustrates a graphical diagram of blended battery capacity for an implantable medical device, according to one embodiment.

FIG. 2 illustrates a graphical diagram of blended battery capacity for an implantable medical device, according to one embodiment. Over a first portion 202 of the life of the battery, battery capacity consumed is measured using a first capacity measuring device (here a coulometer). Measurements from the coulometer and measurements of battery capacity consumed using a second capacity measuring device (here a capacity-by-voltage device) are combined (or capacity-blended) over a second portion of the life of the battery 204. Battery capacity consumed is measured using only the capacity-by-voltage device over a third portion of the life of the battery 206, according to various embodiments.

Figure 7:
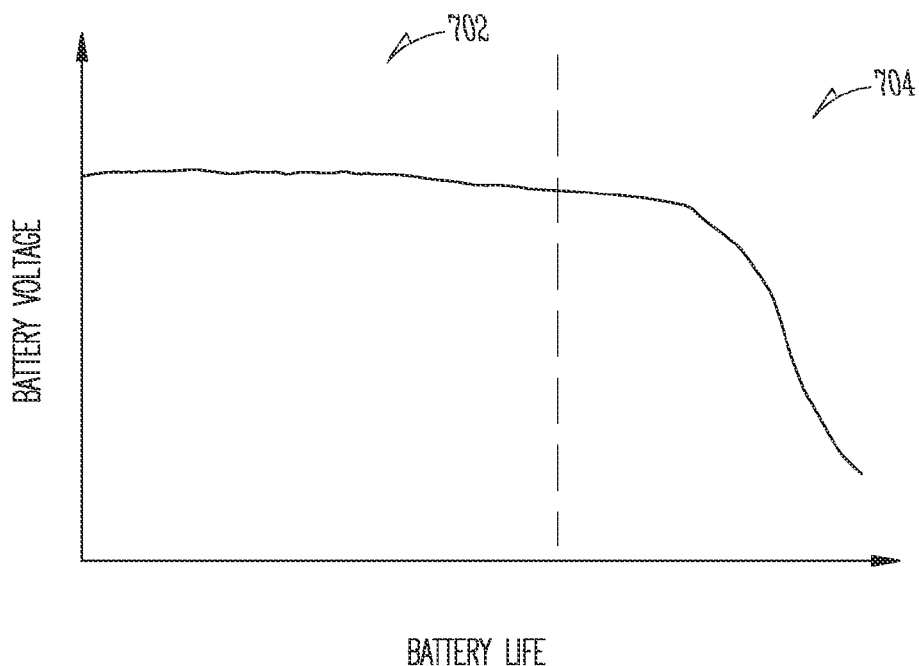
FIG. 7 illustrates a graphical diagram of measured voltage over the life of a battery, according to one embodiment.

Battery capacity consumed can be measured directly with the coulometer and indirectly by measuring voltage. A mapping is used between voltage measured and capacity consumed. FIG. 7 illustrates a graphical diagram of measured voltage over the life of a battery, according to one embodiment. As shown, the coulometer method is better suited for the early portion 702 of the battery's life, where voltage has less resolution. The voltage method is better suited for the later portion 704 of the battery's life.

As shown in FIG. 2, discussed above, measurements of battery capacity derived from the coulometer and measurements of battery capacity derived from the capacity-by-voltage device are "capacity-blended" over a time period. When used herein, capacity-blending refers to using a weighted average the outputs of two or more capacity measuring devices to calculate capacity. Capacity-blending the measurements largely reduces abrupt changes in longevity gauge behavior. According to the embodiment in FIG. 2, at approximately 51% capacity consumed (as measured by the coulometer), blending of the measurements begins. A weighted average is computed to combine the measurements from the coulometer and the capacity-by-voltage device, according to various embodiments. In one embodiment, at 51% capacity consumed, the combination includes 99% of the coulometer measurement and 1% of the capacity-by-voltage measurement, at 62.5% capacity consumed, the combination includes 50% of the coulometer measurement and 50% of the capacity-by-voltage measurement, and at 74% capacity consumed, the combination includes 1% of the coulometer measurement and 99% of the capacity-by-voltage measurement, and in between these points the percentage of each measurement used is linear. Other formulas for combining or capacity-blending the coulometer and capacity-by-voltage measurements of battery capacity are possible, without departing from the scope of this disclosure. In addition, more than two sources of capacity measurements can be combined in this manner, such as software coulometer capacity measurements and charge-time capacity measurements.

According to various embodiments, the system calculates life phase from total capacity, based on measured capacity consumed, average power consumption rate, and a set of constants. The coulometer can be used to measure power, according to various embodiments. According to an embodiment, the coulometer measures capacity in units of Ampere seconds. The difference between two coulometer measurements over a time period is divided by the duration of the time period, and the result is average current (in amperes). Multiplying the average current by the average (or most recently-measured) voltage yields average power. Long-term average power can be used to filter individual power measurements, such as a simple average or moving average. According to various embodiments, battery life phases calculated include, but are not limited to: BOL (beginning of life), OY (one year remaining to explant, Explant (90 days until EOL), ERI (elective replacement indicator, usually the same as Explant), EOL (end of life), and BEX (battery expired). Based on total capacity of the battery model (Qbex) and desired duration of each life phase, trigger points are computed (using the formula $t=Q \times V/P$). For example, if a 90 day period from BOL to BEX is desired, V and P may be measured and Q calculated. Subtracting that value from Qbex yields Qeol. Similarly, if a 150 day period is desired from ERI to EOL, Qeol and Qeri may be calculated. Life phase may then be triggered by comparing the most recent blended capacity (Qi) to the trigger capacity. For example, if Qi>Qeri, then a message indicating ERI is displayed. While this example uses a capacity based system, voltage and charge time may be used without departing from the scope of this disclosure. For fault control, voltage, power and charge time limits exist. According to various embodiments, measuring battery capacity consumed includes measuring battery capacity in units of Ampere-hours (Ahr). According to various embodiments, capacity from a capacity-by-voltage device ($Q_{voltage}$) and capacity from a coulometer ($Q_{coulometer}$) are capacity-blended using the following formula:

$$Q_i = \frac{Q_{i-1} - \frac{Q_{BEX}}{2}}{75\% \times Q_{BEX} - \frac{Q_{BEX}}{2}} \times Q_{Voltage} + \left(1 - \frac{Q_{i-1} - \frac{Q_{BEX}}{2}}{75\% \times Q_{BEX} - \frac{Q_{BEX}}{2}}\right) \times Q_{Coulometer}$$

Other formulas for combining or capacity-blending the coulometer and capacity-by-voltage measurements of battery capacity are possible, without departing from the scope of this disclosure.

According to various embodiments, the implantable medical device (IMD) measures capacity consumed, average power and voltage, and calculates trip points for BEX, EOL, ERI and OY. The IMD compares capacity consumed to capacity trip points to determine life phase, according to varying embodiments. According to one embodiment, three of three calculations over a trip point will trigger a life phase status change. Three calculations are used in this embodiment to filter noise. More or fewer calculations may be used to trigger a life phase status change based on the magnitude of the noise and the ability to pre-filter the noise. According to various embodiments, the IMD reports certain values to an external device having a display (such as the programmer depicted in FIG. 5). Examples of reported values include Qi, Qeri, P and V. The programmer can then compute time to ERI (or time to explant), and can further estimate longevity based on user changes to programming settings such as pace mode, pace pulse width and amplitude, according to various embodiments. According to varying embodiments, time to explant is calculated with an extra allocation for future cap reforms. Time to explant is recalculated if the IMD is reprogrammed (amplitude, pulse width, etc.), according to various embodiments.

According to various embodiments, a hardware-based coulometer is used to monitor power consumption over a specified time interval. Based on these measurements, a system of power alarms can be provided. Before implant, if the IMD exceeds a power consumption limit (75μW over 1 week, for example) for three measurements in a row, a fault is declared and the clinician is instructed not to implant the device, in an embodiment. In one embodiment, if the device exceeds fixed power limits over 20 seconds or 1 day in pre-implant testing, an alarm is set. Post-implant, if the device exceeds expected power over 20 seconds, 1 day, or 1 week, an alarm is set in an embodiment. Alarms are logged by the device but not displayed, in varying embodiments.

A further embodiment of the system includes a coulometer adapted to measure battery capacity consumed in an implantable device. The system embodiment also includes a capacity-by-voltage device adapted to measure battery capacity consumed in the device. The system embodiment further includes means for blending the measurements from the coulometer and the capacity-by-voltage device to determine battery capacity consumed. According to an embodiment, the means for blending includes a computer processor or controller. The means for blending includes software stored in a computer readable medium, according to various embodiments.

According to various embodiments, the controller is adapted to select capacity measurements from the two or more capacity measurement devices, and use only one of the measurements or compute a capacity-blended combination of the measurements, based on such factors as: a predetermined or programmable schedule; predetermined set points; battery parameters; or battery life indicators.

All battery chemistries are subject to depressed voltages following a high power event. Different chemistries will respond differently to the events, exhibiting faster or slower voltage recovery. Certain battery chemistries, CFx and $MnO_2$ in particular, are prone to depressed voltage immediately after a high-power event (wireless telemetry, beeper or charge). Because voltage is used to determine depletion state, it would be possible to erroneously read a low voltage and change life-phase. According to various embodiments, a method is used to prevent measurement of battery voltage during a high-power event, and to subsequently evaluate the change in voltage to ascertain when the battery voltage is recovered from the event. According to various embodiments, the method is used with batteries having battery chemistries applicable for use in implantable devices.

Before being implanted, the implantable device may be subject to cold temperatures. Depending on battery chemistry and device model, low temperature may cause low monitoring voltage, long charge time, or inability to communicate via wireless radio frequency (RF) or inductive telemetry. According to various embodiments, the device has built-in temperature limits to warn the user of long charge times or the inability to establish communications. After the device is implanted, lead impedance, pace counts and sense counts are measured and averaged on a periodic basis, according to varying embodiments. In various embodiments, lead impedance, pace counts and sense counts can be used to predict time to explant and limits for power alarms.

System for Displaying Battery Longevity

Figure 3:
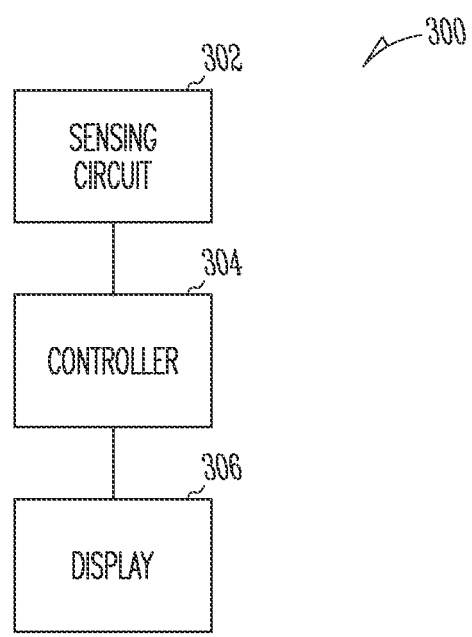
FIG. 3 illustrates a block diagram of a system for displaying battery longevity, according to one embodiment.

FIG. 3 illustrates a block diagram of a system for displaying battery longevity, according to one embodiment. One of ordinary skill in the art will appreciate that this system is a subsystem of the one depicted in FIG. 1, in various embodiments. The system 300 includes a sensing sub-system, or sensing circuit 302, adapted to measure remaining battery capacity for an implantable device. The system embodiment also includes a controller 304 connected to the sensing circuit, or sensing sub-system. The controller is adapted to calculate battery longevity based on measured capacity. The system embodiment further includes a display 306 in communication with the controller, display adapted to depict battery longevity shown in units of time remaining in the life of the battery. According to an embodiment, the display is adapted to depict a semicircular gauge with battery longevity. According to another embodiment, the display is adapted to depict a graph showing battery longevity. Other types of displays showing units of time remaining in the life of the battery are possible without departing from the scope of the disclosure. The system also has the capability to display battery capacity in units of Ahr, according to various embodiments.

The display is part of a programmer, such as depicted in FIG. 5 below, in an embodiment. The sensing circuit is located within the implantable device, in various embodiments. The controller may be located within the implantable device, within the programmer, or controller function may be shared between the device and programmer in various embodiments. According to an embodiment, the controller may be located in a computing system separate from the device and programmer.

According to various embodiments, the display depicts battery longevity using a "gas gauge" display, including a semi-circle time remaining gauge with a 1-year remaining pie-slice (see FIGS. 8A-8D, discussed below). A "time to explant" gauge is used in the depicted embodiment. In addition, the display includes numeric capacity remaining and power consumption, according to various embodiments. In one embodiment, a graph is used to depict battery longevity (see FIG. 8E, discussed below). Benefits of a time remaining gauge include a full-scale representation of fixed longevity for all devices of the same model number, and that the one-year remaining trigger point on the gauge is fixed for a given model number. According to various embodiments, battery capacity consumed includes battery capacity in units of Ampere-hours (Ahr).

A further embodiment of the system includes means for sensing remaining battery capacity for an implantable device. The system embodiment also includes means for calculating battery longevity based on sensed capacity, the calculating means connected to the sensing means. The system embodiment further includes a display connected to the calculating means, the controller and the display adapted to cooperate to depict battery longevity in units of time remaining in the life of the battery. According to various embodiments, the sensing means includes a coulometer. The sensing means includes a capacity-by-voltage device, in various embodiments. Other types of sensing means can be used without departing from the scope of this disclosure. In one embodiment, the calculating means includes a microprocessor. Other types of calculating means can be used without departing from the scope of this disclosure. One of ordinary skill in the art will understand that, the calculating means shown and described herein can be implemented using software, hardware, and combinations of software and hardware.

Implantable Medical Devices

Figure 4:
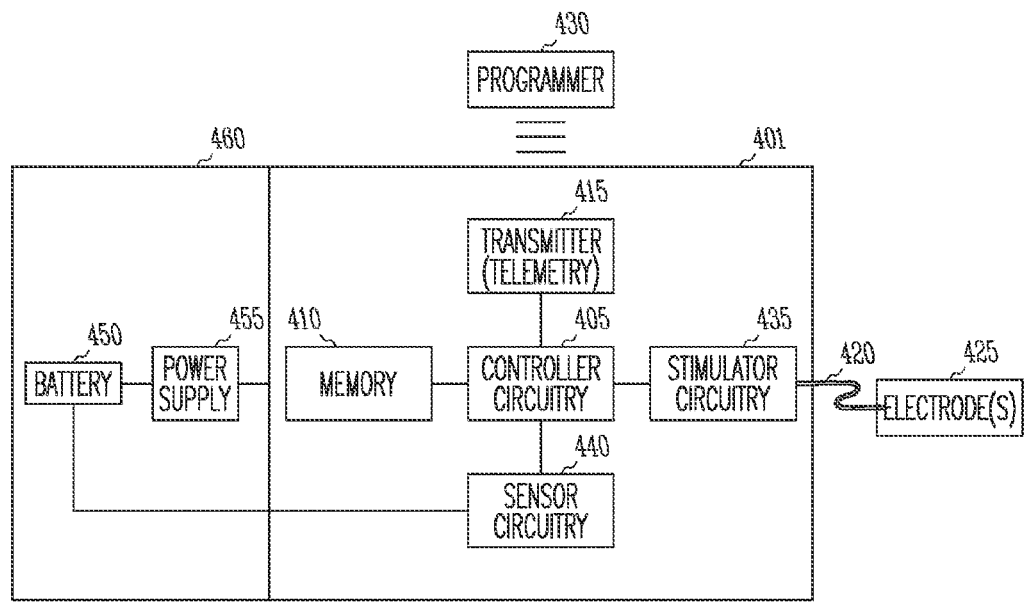
FIG. 4 illustrates a block diagram of a system with an implantable medical device (IMD), according to one embodiment.

FIG. 4 illustrates a block diagram of a system with an implantable medical device (IMD), according to one embodiment. The system includes an IMD 401, an electrical lead 420 coupled to the IMD 401, and at least one electrode 425. The IMD includes a controller circuit 405, a memory circuit 410, a wireless telemetry circuit 415, and a stimulation circuit 435. The controller circuit 405 is operable on instructions stored in the memory circuit to deliver an electrical stimulation therapy. Therapy is delivered by the stimulation circuit 435 through the lead 420 and the electrode(s) 425. The wireless telemetry circuit 415 allows communication with an external programmer 430. The programmer 430 can be used to adjust the programmed therapy provided by the IMD 401, and the IMD can report device data (such as battery capacity remaining and lead resistance) and therapy data (such as sense and stimulation data) to the programmer using wireless telemetry, for example. The illustrated system also includes sensor circuitry 440 that is adapted to measure capacity consumed for a device battery 450, according to the method of FIG. 6B, for example. The battery 450 is connected to device 401 via power supply circuitry 455, and is housed together in device 401, or in a battery housing 460 adjacent the device 401, according to various embodiments. The controller circuit 405 processes sensor data from the sensor circuitry and calculates battery capacity, according to the disclosed methods. According to various embodiments, the disclosed systems and methods can be used with a leadless device. For example, in an embodiment, one or more satellite electrodes are controlled wirelessly to deliver electrical therapy.

One of the many applications for dynamic battery management systems incorporating one or more teachings of the present subject matter includes an implantable heart monitor. As used herein, implantable heart monitor includes any implantable device for providing therapeutic stimulus to a heart muscle. Thus, for example, the term includes a pacemaker, a cardioverter/defibrillator, a cardiac resynchronization therapy (CRT) device, a neurostimulator, a congestive heart failure device, and combinations and permutations thereof. An implantable heart monitor includes a lead system, which after implantation electrically contact strategic portions of a patient's heart. Portions of the monitor include a monitoring circuit for monitoring heart activity through one or more of the leads of lead system, and a therapy circuit for delivering electrical energy through one or more of the leads to a heart. The monitor also includes an energy storage component, which includes a battery and at least one capacitor.

FIG. 5 illustrates a block diagram of a programmer such as illustrated in the system of FIG. 4 or other external device to communicate with the IMD(s), according to one embodiment. FIG. 5 illustrates a programmer 544, such as the programmer 430 illustrated in the system of FIG. 4 or other external device to communicate with the implantable medical device(s), according to one embodiment. Examples of other external devices include, but are not limited to, Personal Digital Assistants (PDAs), personal laptop and desktop computers, or handheld devices. The illustrated device 544 includes controller circuitry 545 and a memory 546. The controller circuitry 545 is capable of being implemented using hardware, software, and combinations of hardware and software. For example, according to various embodiments, the controller circuitry 545 includes a processor to perform instructions embedded in the memory 546 to perform a number of functions, including communicating data and/or programming instructions to the implantable devices. The illustrated device 544 further includes a transceiver 547 and associated circuitry for use to communicate with an implantable device. Various embodiments have wireless communication capabilities. For example, various embodiments of the transceiver 547 and associated circuitry include an antenna for use to wirelessly communicate with an implantable device. The illustrated device 544 further includes a display 548, input/output (I/O) devices 549 such as a keyboard or mouse/pointer, and a communications interface 550 for use to communicate with other devices, such as over a communication network. The display 548 can be used to display battery longevity for a battery in the IMD, according to various embodiments.

Methods for Battery Measurement Capacity-Blending

Figure 6A:
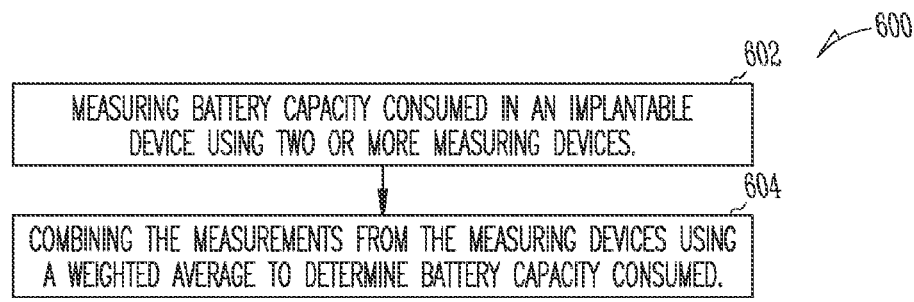
FIG. 6A illustrates a flow diagram of a method of combining measured battery capacity for a battery in an implantable medical device, according to one embodiment.

FIG. 6A illustrates a flow diagram of a method of combining measured battery capacity for a battery in an implantable medical device, according to one embodiment. According to an embodiment of the method 600, battery capacity consumed in an implantable device is measured using two or more measuring devices, at 602. According to the embodiment, the measurements from measuring devices are combined using a weighted average to determine battery capacity consumed, at 604.

According to various embodiments, measuring battery capacity consumed includes measuring battery capacity using a coulometer, a capacity-by-voltage device, a software coulometer, or a charge-time measuring device (which uses a look-up table to convert charge-time to capacity consumed or remaining, as discussed above). Battery capacity consumed is measured continuously, daily, hourly, or in a variety of frequencies, according to various embodiments. Battery capacity consumed is reported to a controller daily, hourly, or in a variety of frequencies, according to various embodiments. Measuring battery capacity consumed using a coulometer includes measuring battery capacity using a coulometer that is calibrated for accuracy, in an embodiment. According to various embodiments, measuring battery capacity consumed includes measuring battery capacity in units of Ampere-hours (Ahr).

Figure 6B:
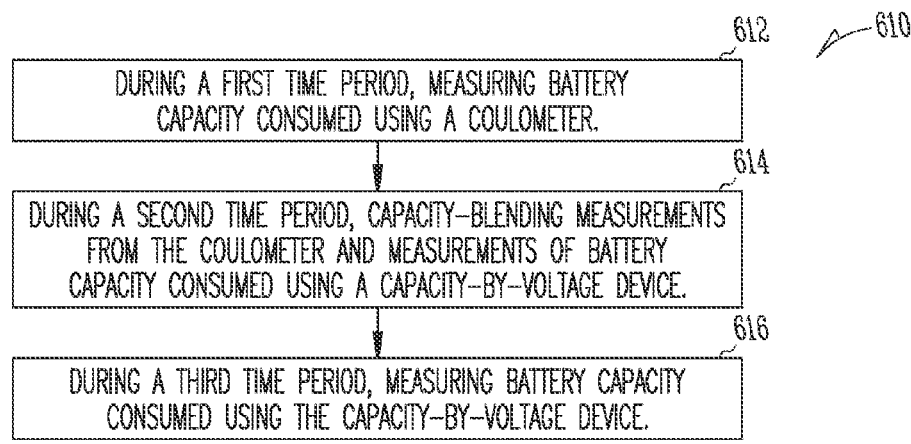
FIG. 6B illustrates a flow diagram of a method for measuring capacity consumed for a battery in an implantable medical device, according to one embodiment.

FIG. 6B illustrates a flow diagram of a method for measuring capacity consumed for a battery in an implantable medical device, according to one embodiment. According to an embodiment of the method 610, battery capacity consumed is measured using a coulometer during a first time period, at 612. Measurements from the coulometer and measurements of battery capacity consumed using a capacity-by-voltage device are capacity-blended during a second time period, at 614. Battery capacity consumed is measured using the capacity-by-voltage device during a third time period, at 616.

According to varying embodiments, the first time period begins at the beginning of life of the battery and ends when the battery has 50% capacity consumed. The second time period begins when the battery has 50% capacity consumed and ends when the battery has 75% capacity consumed, according to various embodiments. According to various embodiments, the third time period begins when the battery has 75% capacity consumed and ends when the battery capacity expires. Other measures can be used to define the time periods, without departing from the scope of this disclosure. As discussed above, capacity-blending measurements from the coulometer and the capacity-by-voltage device may include computing a weighted average of the measurements in various embodiments. The computed weighted average includes a linear weighted average, in some embodiments. According to an embodiment, measuring battery capacity consumed using the capacity-by-voltage device includes using a look-up table.

Methods for Displaying Battery Longevity

Figure 6C:
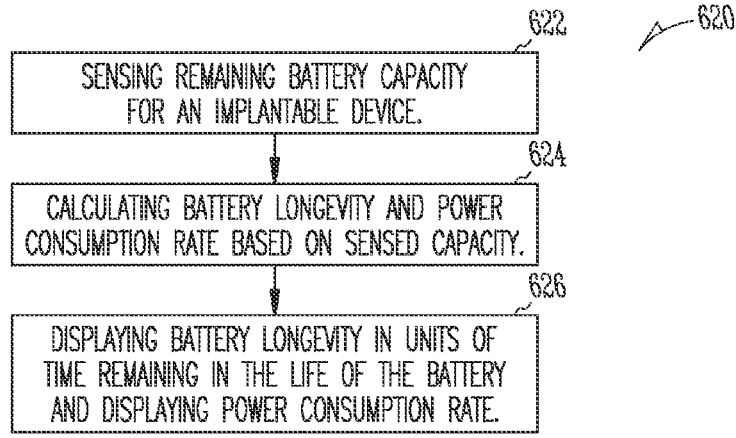
FIG. 6C illustrates a flow diagram of a method for displaying battery longevity for a battery in an implantable medical device, according to one embodiment.

FIG. 6C illustrates a flow diagram of a method for displaying battery longevity for a battery in an implantable medical device, according to one embodiment. According to an embodiment of the method 620, remaining battery capacity for an implantable device is sensed, at 622, and battery longevity calculated based on the sensed capacity, at 624. Battery longevity is displayed in units of time remaining in the life of the battery in the form of a semi-circular gauge, at 626.

According to an embodiment, the method also includes calculating power consumption rate using a coulometer, and displaying the power consumption rate. According to various embodiments, sensing remaining battery capacity includes using a coulometer to measure capacity. Sensing remaining battery capacity includes using a capacity-by-voltage device to measure capacity, according to varying embodiments. According to various embodiments, sensing remaining battery capacity includes using a capacity-by-voltage device and a coulometer to measure capacity. In an embodiment, the measurements from the capacity-by-voltage device and the coulometer are capacity-blended to determine battery capacity consumed. According to various embodiments, the method also includes calculating battery life phase from sensed capacity.

Figure 6D:
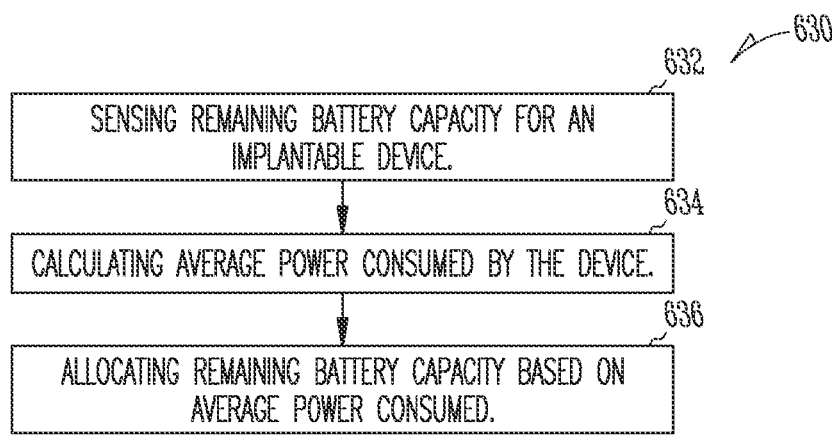
FIG. 6D illustrates a flow diagram of a method for dynamically allocating capacity for a battery in an implantable medical device, according to one embodiment.

FIG. 6D illustrates a flow diagram of a method for dynamically allocating capacity for a battery in an implantable medical device, according to one embodiment. According to an embodiment of the method 630, remaining battery capacity is sensed for an implantable device, at 632. Average power consumed by the device is calculated at 634, in an embodiment. In this embodiment, remaining battery capacity is allocated based on average power consumed, at 636. According to various embodiments, calculating average power consumed includes reporting average power consumed periodically, such as daily, hourly or weekly.

According to various embodiments, average power consumed is used to create a dynamic system that allocates capacity between an explant indicator (in units of measured capacity) and cessation of therapy. The display provides feedback to a clinician so that the clinician can observe the decreased longevity resulting from overly aggressive programming, according to various embodiments.

Figure 8A:
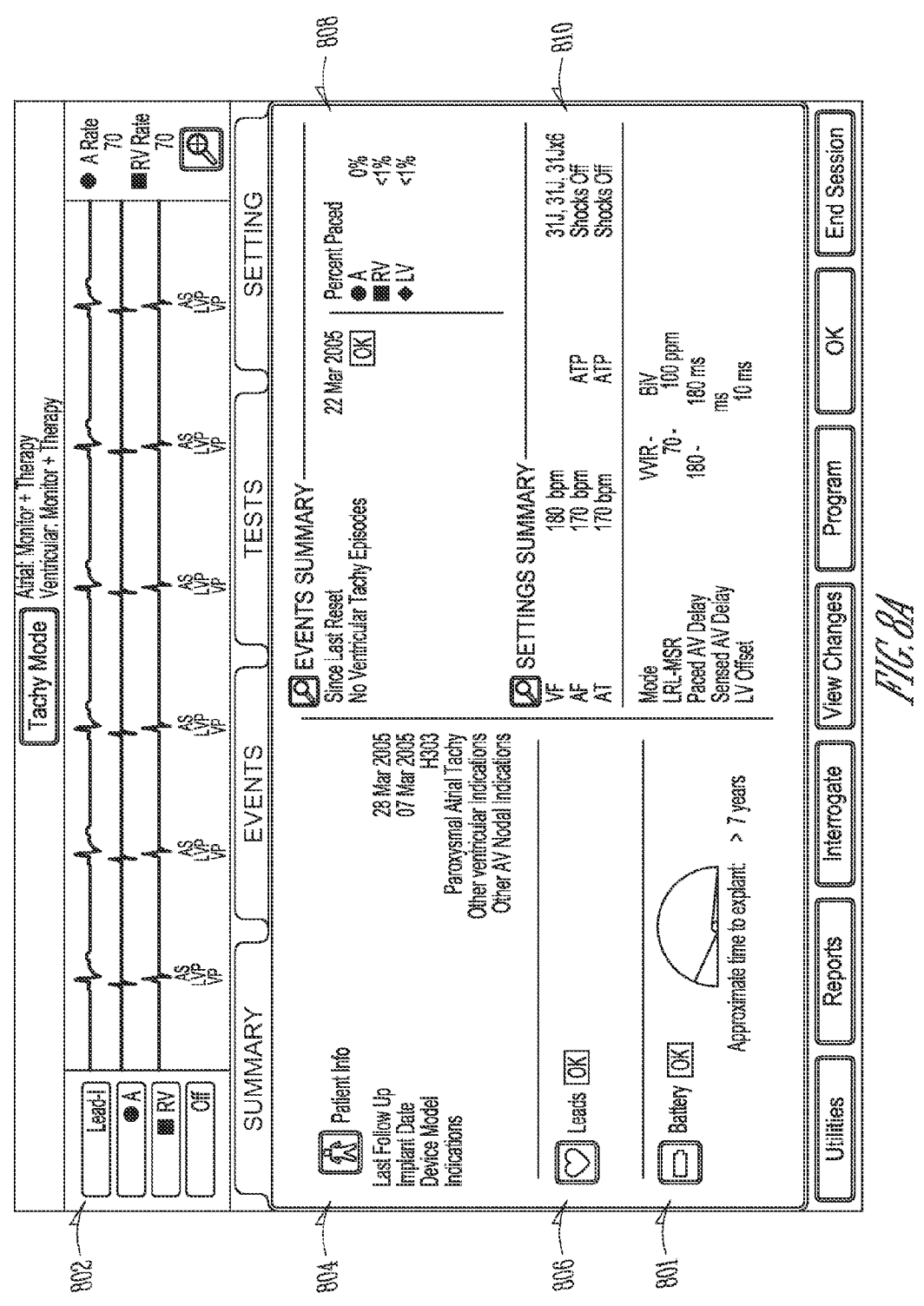
Figure 8B:
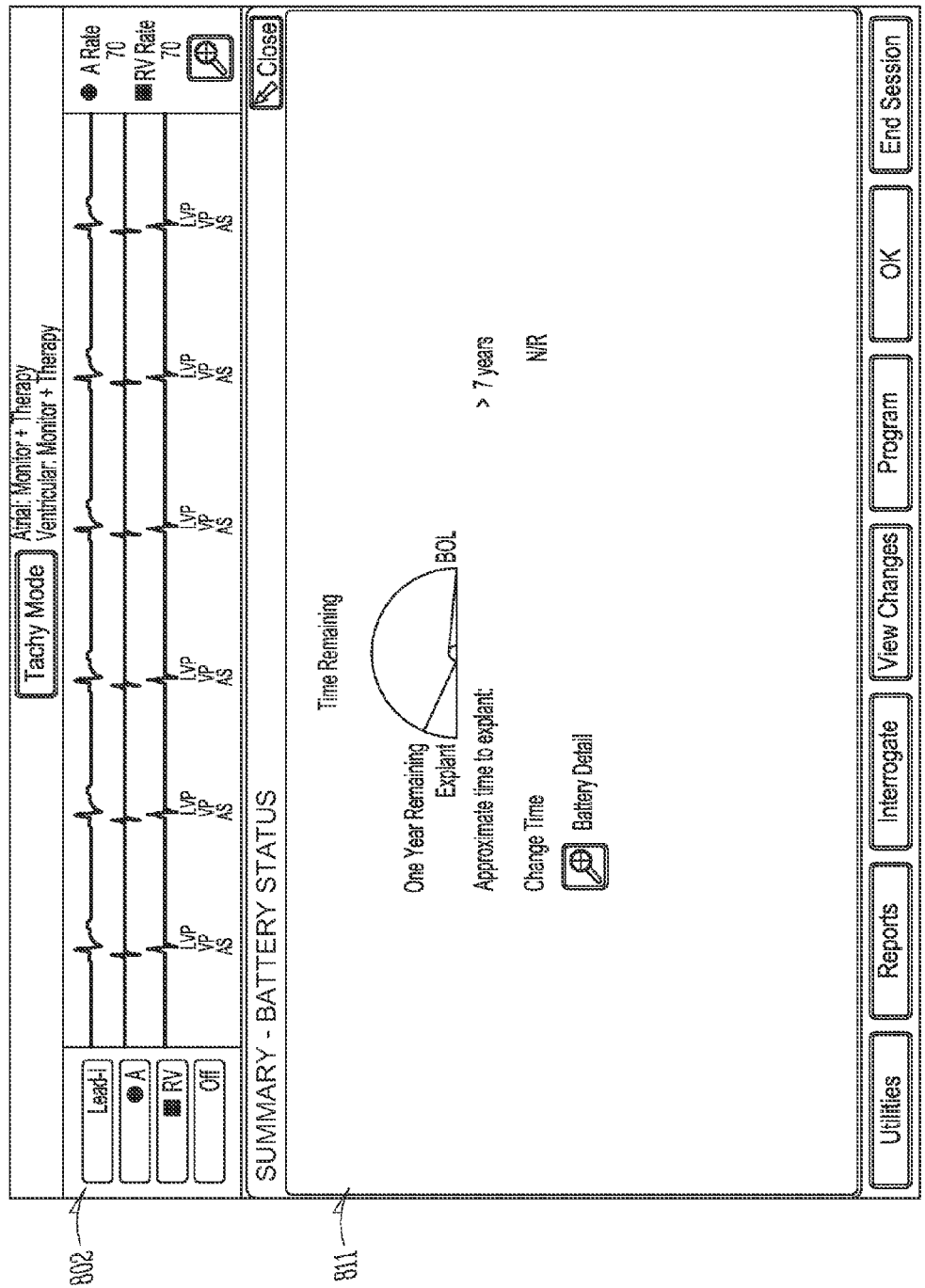

FIGS. 8A-8E illustrate screen displays for the system of FIG. 3, used to display battery longevity, according to one embodiment. As discussed with respect to the method of FIG. 6C, battery longevity is displayed in units of time remaining in the life of the battery. FIG. 8A illustrates a screen display including a lead signal display 802, a patient information display 804, a lead status display 806, a battery status display 801, an events summary display 808, and a settings summary display 810.

Figure 8C:
Figure 8D:
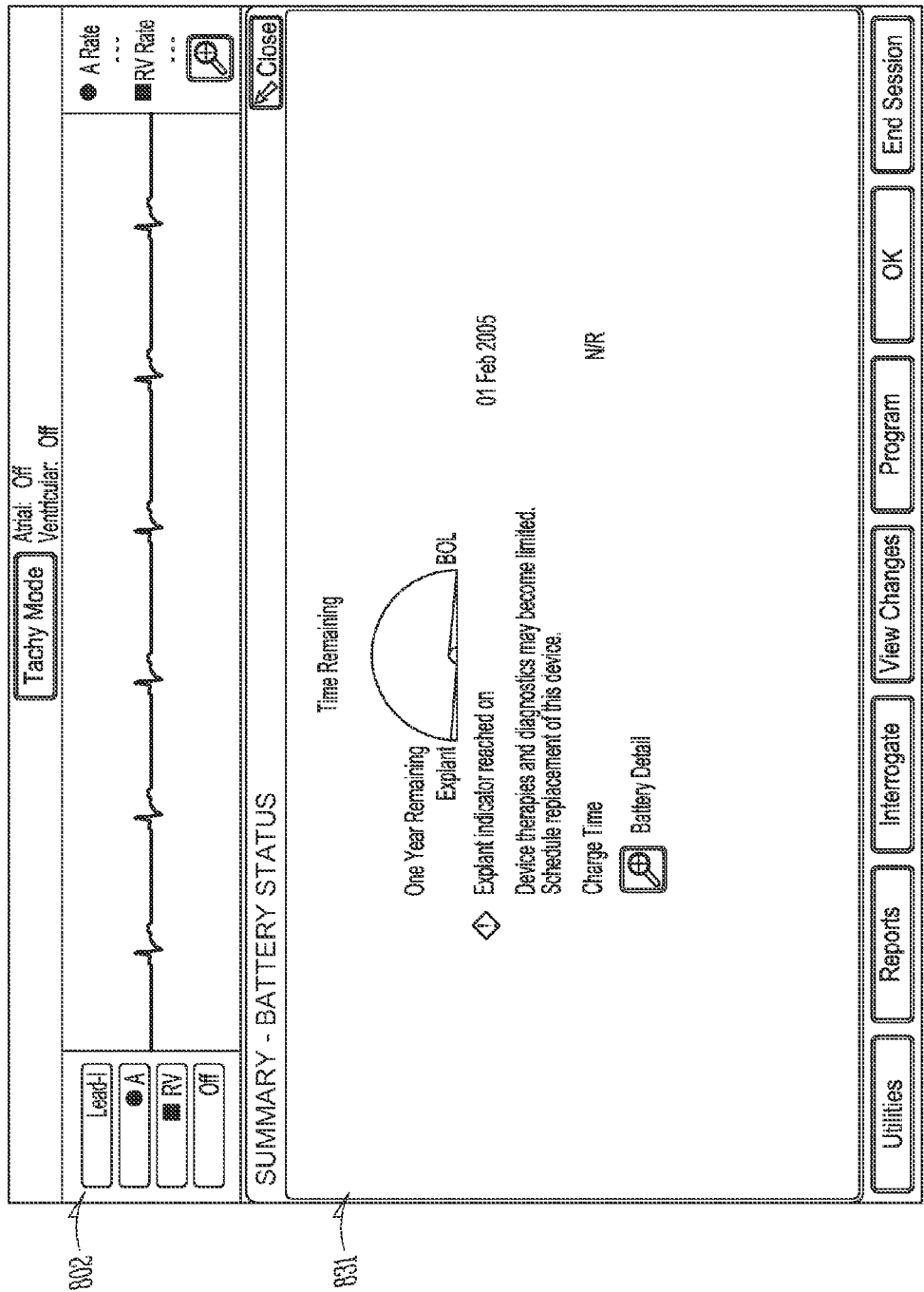

The battery status display 801 includes a "gas gauge" type (or semi-circular gauge) graphic 803 with a needle to depict the battery longevity. Battery longevity is also displayed with text 805, conveying the remaining battery life in units of time. The battery status display 801 further includes a button for battery status, according to an embodiment. Other types of battery longevity displays are within the scope of this disclosure. FIG. 8B illustrates a screen display of battery status screen 811 including the lead signal display. FIG. 8C illustrates a screen display of battery detail screen 821. The battery detail screen 821 shows average power and capacity consumed, according to an embodiment. Lead signal display 802 is also depicted. FIG. 8D illustrates a battery status screen 831 including a one-year to explant indicator, similar to the screen of FIG. 8B. In FIG. 8D, however, the gauge indicates that the battery has reached its explant indicator.

Figure 8E:
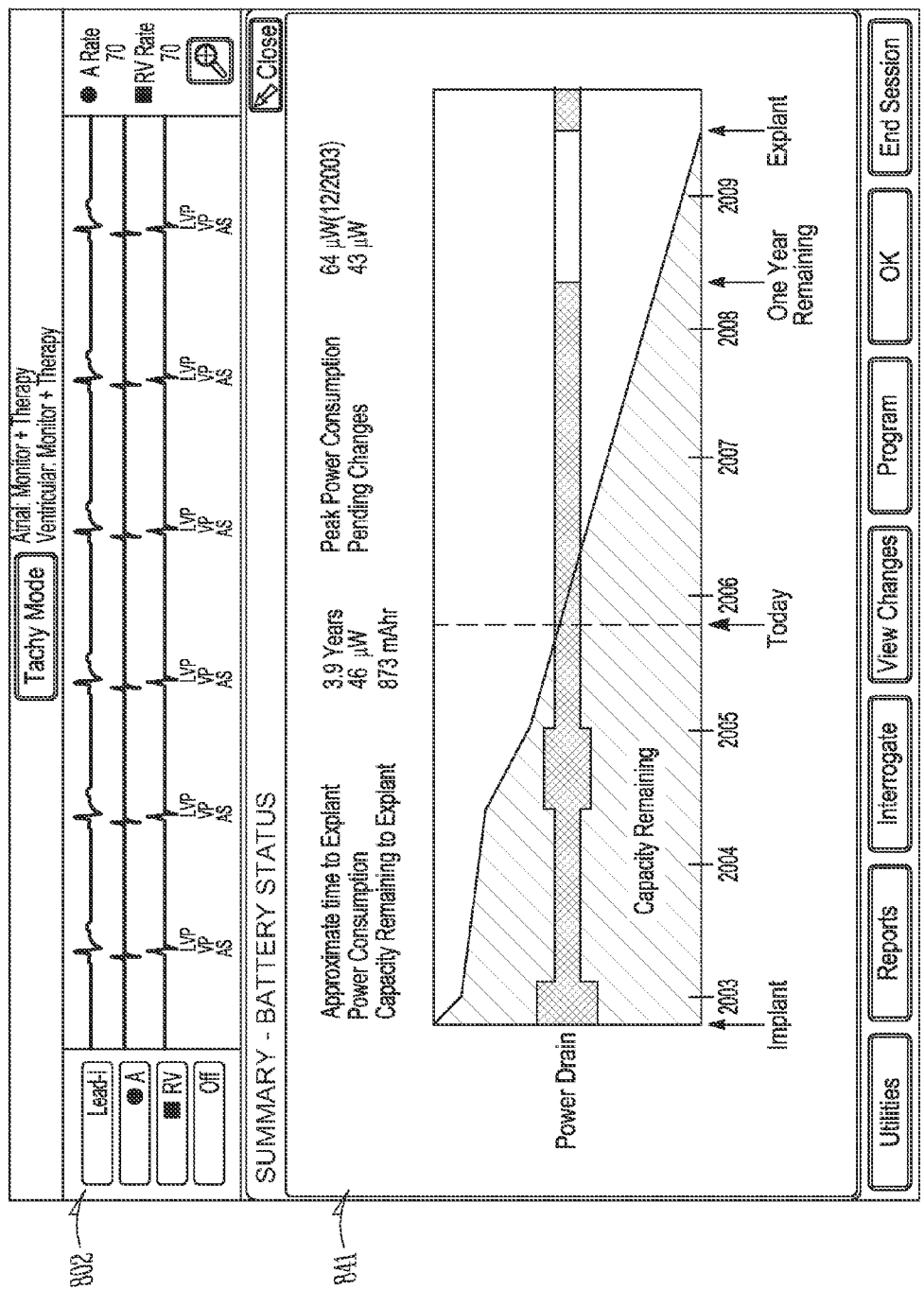

FIG. 8E illustrates a screen display of battery status screen 841, where the battery capacity remaining is depicted in graphic format. The graph includes a rectangular timeline with the left side indicating implant and the right explant. In addition, a present status indicator and a 1-year to explant indicator are included, in an embodiment. In addition, thickness of a line on the graph can be used to indicate the rate of power consumption, in various embodiments. A cumulative capacity remaining line chart may also be included, and can change dynamically in response to programming changes to show predicted or future power consumption and time to explant. Other shapes and types of battery longevity displays are within the scope of this disclosure.

Determining Depth of Discharge

Battery voltage recovery can be used as in indicator of battery depth of discharge in an implantable device. Depth of discharge refers to the amount of energy withdrawn from a battery relative to how much could be withdrawn if the battery were discharged until exhausted. In one embodiment, battery voltage recovery is measured after a high voltage charge and is compared against a requirement curve to determine battery depth of discharge. In another embodiment, measured battery voltage recovery is compared with a stored population of other implanted devices to determine battery depth of discharge.

Voltage recovery varies with high power (high voltage) events and battery depth of discharge. Implantable devices have periodic maximum energy reforms (constant energy) and regular subsequent voltage measurements, in various embodiments. In one embodiment, voltage recovery is evaluated along with coulometer measurements and absolute voltage measurements to more precisely determine depth of discharge. The voltage recovery data is blended with coulometer and capacity-by-voltage measurements to determine battery life phase and time remaining to explant, in various battery management embodiments. A programmer or other external device is used to collect long-term and statistical population data relating to voltage recovery, and the data is compared to identify individual battery faults and/or overall trends, in various embodiments. Outlier devices, or devices that have voltage recovery curves inconsistent with population averages, can be identified and faults in voltage measurement, coulometer measurement, and/or faulty bypass capacitors can be identified.

Implantable medical devices have maximum energy charges throughout the course of battery life. In one embodiment, devices have maximum energy charges at least once per quarter. Battery voltage measurements occur at a programmable time after charges and at programmable intervals thereafter, in various embodiments. In one embodiment, battery voltage measurements occur within 21 hours after maximum energy charges and on 21 hour intervals thereafter, with some exceptions, in an embodiment. The present subject matter uses a measure of voltage recovery, such as $dV/dt$, as a map of depth of depletion. Voltage recovery data can be blended with capacity-by-voltage and coulometer measurements for increase fault tolerance and precision of the capacity estimate, in various embodiments.

Figure 9:
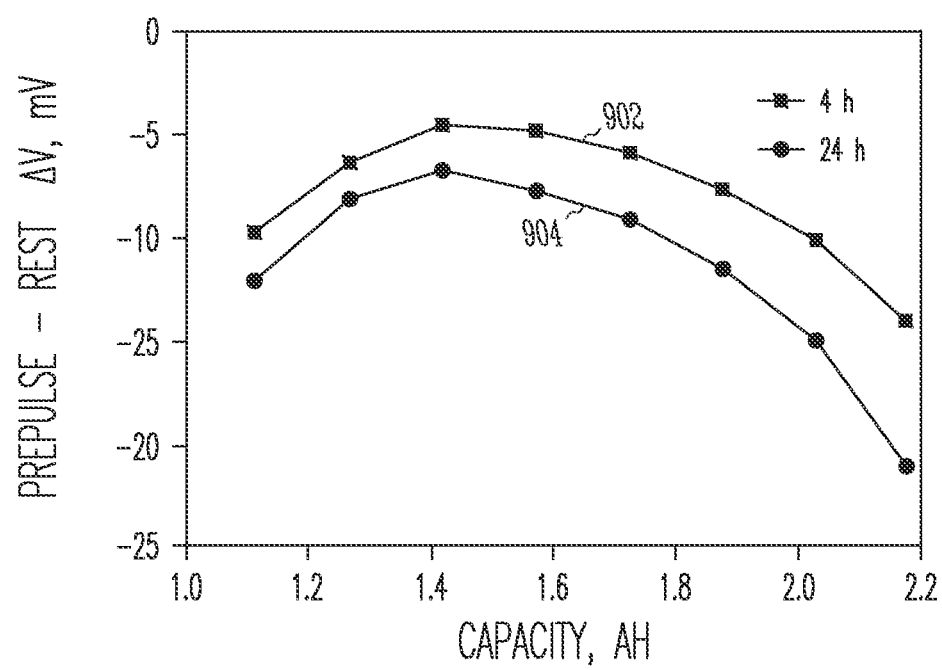
FIG. 9 illustrates a graphical diagram of voltage recovery for determining depth of discharge of a battery in an implantable medical device, according to various embodiments.

FIG. 9 illustrates a graphical diagram of voltage recovery for determining depth of discharge of a battery in an implantable medical device, according to various embodiments. The graphical diagram plots change in voltage ($\Delta V$) of the battery from pre-maximum energy charge of the device. The depicted embodiment shows plotted measurements over a three year span of battery life. The three year span is an example, other time periods may be used without departing from the scope of the disclosure. Three year data is a common template for comparing data. Historically, battery data is available at intervals of 1, 3, 5, and 7 years. In some batteries, the entire capacity can be depleted in that time frame. For some device batteries that should last 5-10 years, three year data is usually the best available data. The depicted embodiment includes a first curve 904 showing measurements four hours after maximum charge and a second curve 902 showing measurements twenty-four hours after maximum charge. In various embodiments, maximum charge is defined as maximum energy tachy charge. Quarterly reforms are most effective if charging is to the same as maximum tachy therapy charge. The maximum energy varies by device model. HE (high energy) devices charge to ~36 J while SE (standard energy) devices charge to 27-30 J. Other periods of measurement can be used without departing from the scope of the disclosure. The separation between the curves is an indication of voltage recovery for the device over the life of the battery.

Figure 10:
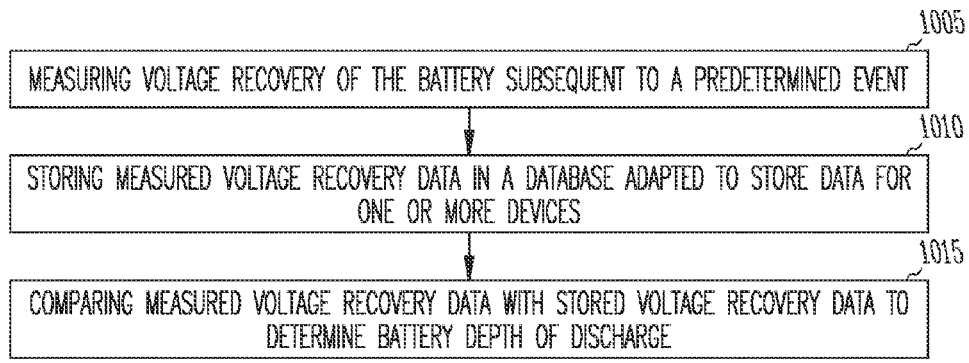
FIG. 10 illustrates a flow diagram of a method for determining depth of discharge for a battery in an implantable medical device, according to one embodiment.

FIG. 10 illustrates a flow diagram of a method for determining depth of discharge for a battery in an implantable medical device, according to one embodiment. At 1005, voltage recovery of the battery is measured subsequent to a predetermined event. According to various embodiments, voltage recovery is measured seconds after the event. Voltage recovery can also be measured more (sub-seconds) or less (hours) frequently, in various embodiments. Measured voltage recovery data is stored in a database adapted to store data for one or more devices, at 1010. Measured voltage recovery data is compared with stored voltage recovery data to determine battery depth of discharge, at 1015. According to various embodiments, determining battery depth of discharge includes collecting voltage recovery data on a large sample of cells. For example, voltage is measured before a simulated HV charge and four hours later. The data is linear and shows that at 25% depletion, the difference between before and after voltage is 25 mV, at 50% depletion, the voltage difference is 50mV, and at 75% depletion, the voltage difference is 75 mV, in one example. In an implanted device, voltage recovery is also measured by sensing voltage before an HV charge and 4 hours later. The device uses a look-up table to determine the depletion based on voltage difference. In this example, 51 mV would correspond to 51% depletion. In various embodiments, absolute capacity (Ah or mAh) is used rather than relative depletion (% depletion). $MnO_2$ battery chemistries exhibit non-monotonic data, in an embodiment. The recovery voltage for $MnO_2$ batteries is low at beginning of life, then rises, and then falls near ERI then increases. Therefore, other methods (coulometer, voltage by capacity, charge time, etc.) are used to determine device depletion for $MnO_2$ batteries, in various embodiments. According to various embodiments, battery capacity consumed is measured using a coulometer and using a capacity-by-voltage device. Measured battery capacity consumed is combined with measured voltage recovery data using a predetermined weighted average, and the combined data is stored in the database. The stored data is used to determine battery depth of discharge, according to an embodiment.

In one embodiment, measuring voltage recovery includes mapping voltage recovery over time for the device. Comparing measured voltage recovery data with stored voltage recovery data includes comparing measured voltage using a look-up table, in an embodiment. Storing voltage recovery data includes collecting long-term population data, including collecting data for comparison to identify individual device faults and/or to identify device trends, in various embodiments. In one embodiment, the method further includes measuring battery capacity consumed using a coulometer and combining measured battery capacity consumed with measured voltage recovery data using a predetermined weighted average. The combined data is stored in the database and used to determine battery depth of discharge. In another embodiment, the method also includes measuring battery capacity consumed using a capacity-by-voltage device and combining measured battery capacity consumed with measured voltage recovery data using a predetermined weighted average. The combined data is stored in the database and used to determine battery depth of discharge. Voltage recovery is stored in a programmer memory, or other external device memory, in an embodiment. Individual device data is also stored in the implantable device memory, in an embodiment.

Figure 11:
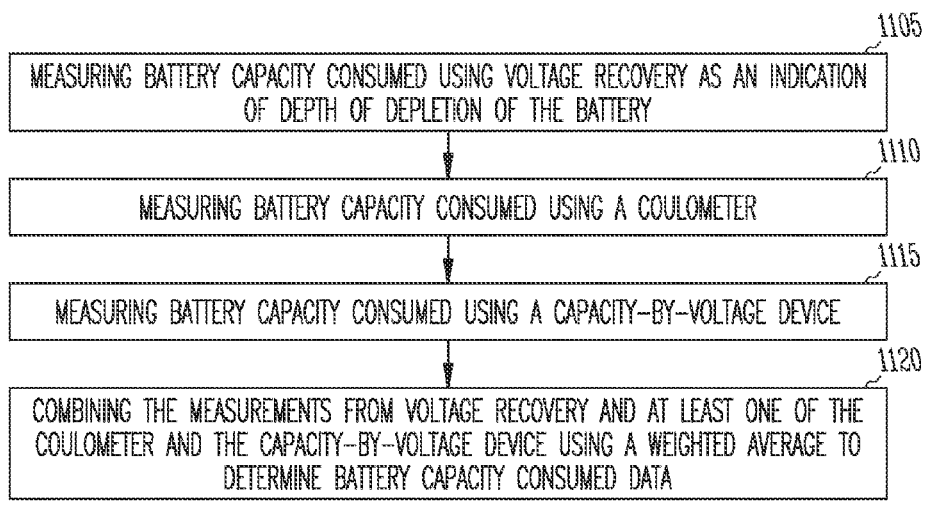
FIG. 11 illustrates a flow diagram of a method for determining capacity consumed for a battery in an implantable medical device, according to one embodiment.

FIG. 11 illustrates a flow diagram of a method for determining capacity consumed for a battery in an implantable medical device, according to one embodiment. At 1105, battery capacity consumed is measured using voltage recovery as an indication of depth of depletion of the battery. Battery capacity consumed is also measured using a coulometer, at 1110. Battery capacity consumed is further measured using a capacity-by-voltage device, at 1115. At 1120, the measurements from voltage recovery and at least one of the coulometer and the capacity-by-voltage device are combined using a weighted average to determine battery capacity consumed data. In an embodiment, all three measurements (voltage recovery, coulometer and capacity-by-voltage) are combined using a weighted average to determine battery capacity consumed. According to various embodiments, the method also includes storing the battery capacity consumed data in a database, and using the stored data to determine battery depth of discharge. Determining battery depth of discharge can include using a look-up table of stored battery capacity consumed data for one or more devices, in various embodiments.

In one embodiment, the stored population data is mapped for the devices to identify individual device faults.

The system of FIGS. 4 and 5 can be adapted for determining depth of discharge for a battery in an implantable medical device. An embodiment of the system includes at least one voltage sensor 440 adapted to sense voltage of the battery 450 and a memory 546 (and/or 410) adapted to store voltage recovery data subsequent to a voltage discharge event from one or more implantable devices 401. The system also includes a controller 545 (and/or 405) connected to the memory and in communication with the implantable medical device. The controller is adapted to measure voltage recovery based on sensed voltage, to store voltage recovery data in the memory, and to compare measured voltage recovery data with stored voltage recovery data to determine battery depth of discharge. According to various embodiments, the memory and controller are incorporated into an external device, such as a programmer or other monitoring device, in communication with the implantable device. The voltage sensor is integrated into the implantable medical device, in various embodiments. In one embodiment, the memory includes a patient follow-up database.

The proposed system for measuring battery depth of discharge has several advantages. By consolidating data from multiple implanted devices, battery performance for the devices can be tracked for specific models of both batteries and devices, to determine acceptable limits and voltage versus capacity profiles. In addition, by comparing individual device battery data with the population, added redundancy and fault tolerance are obtained.

Although specific embodiments have been illustrated and described herein, it will be appreciated by those of ordinary skill in the art that any arrangement which is calculated to achieve the same purpose may be substituted for the specific embodiment shown. This application is intended to cover adaptations or variations of the present subject matter. It is to be understood that the above description is intended to be illustrative, and not restrictive. Combinations of the above embodiments, and other embodiments will be apparent to those of skill in the art upon reviewing the above description. The scope of the present subject matter should be determined with reference to the appended claims, along with the full scope of equivalents to which such claims are entitled.

We claim:

1. A method for determining depth of discharge for a battery in an implantable medical device, comprising:
    measuring voltage recovery and battery capacity consumed of the battery subsequent to a predetermined event;
    storing the measured voltage recovery data and battery capacity consumed in a database adapted to store data for multiple implantable medical device batteries;
    combining the measured battery capacity consumed with the measured voltage recovery data using a predetermined weighted average, the average weighted based on capacity consumed;
    storing the combined data in the database; and
    comparing the measured voltage recovery data, the measured battery capacity consumed, and the combined data with stored data to determine battery depth of discharge.

2. The method of claim 1, wherein measuring voltage recovery includes mapping voltage recovery over time for the device.

3. The method of claim 1, wherein comparing measured voltage recovery data with stored voltage recovery data includes comparing measured voltage using a look-up table.

4. The method of claim 1, wherein storing voltage recovery data includes collecting long-term population data.

5. The method of claim 4, wherein collecting long-term population data includes collecting data for comparison to identify individual device faults.

6. The method of claim 4, wherein collecting long-term population data includes collecting data for comparison to identify device trends.

7. The method of claim 1,
wherein measuring battery capacity consumed includes using a coulometer.

8. The method of claim 1,
wherein measuring battery capacity consumed includes using a capacity-by-voltage device.

9. The method of claim 1,
wherein measuring battery capacity consumed includes using a coulometer and a capacity-by-voltage device.

10. The method of claim 1, wherein storing measured voltage recovery data includes storing data in a programmer memory.

11. The method of claim 1, wherein storing measured voltage recovery data in the database includes storing data in an implantable medical device memory.

12. The method of claim 1, wherein comparing measured voltage recovery data with stored voltage recovery data includes using a controller.

13. The method of claim 12, wherein the controller includes a programmer controller.

14. The method of claim 1, wherein measuring voltage recovery of the battery includes using a voltage sensor to measure voltage recovery of the battery.

15. The method of claim 14, wherein the voltage sensor is integrated into the implantable medical device.

16. The method of claim 1, wherein measuring voltage recovery of the battery includes measuring battery voltage at programmable intervals.

17. A method for determining depth of discharge for a battery in an implantable medical device, comprising:
mapping voltage recovery of the battery over time subsequent to a predetermined event;
measuring battery capacity consumed of the battery;
storing the mapped voltage recovery data and the measured battery capacity consumed in a memory adapted to store data for more than one implantable medical device battery;
combining measured battery capacity consumed with mapped voltage recovery data using a predetermined weighted average, the average weighted based on capacity consumed;
storing the combined data in the memory adapted to store data for more than one implantable medical device battery; and
comparing the combined data with stored data using a look-up table to determine battery depth of discharge.

18. The method of claim 17, wherein storing voltage recovery data includes collecting long-term population data.

19. The method of claim 18, wherein collecting long-term population data includes collecting data for comparison to identify individual device faults.

20. The method of claim 18, wherein collecting long-term population data includes collecting data for comparison to identify device trends.

* * * * *